US008971606B2

(12) United States Patent
Chaoui et al.

(10) Patent No.: US 8,971,606 B2
(45) Date of Patent: Mar. 3, 2015

(54) METHOD FOR AUTOMATICALLY IDENTIFYING THE CONTOURS OF A PREDEFINED BONE, DERIVED METHODS AND CORRESPONDING COMPUTER PROGRAM PRODUCTS

(75) Inventors: Jean Chaoui, Locmaria Plouzane (FR); Stéphane Lavallee, Saint Martin d'Urtage (FR)

(73) Assignee: IMASCAP, Plouzane (FR)

( * ) Notice: Subject to any disclaimer, the term of this patent is extended or adjusted under 35 U.S.C. 154(b) by 85 days.

(21) Appl. No.: 13/704,930

(22) PCT Filed: Jun. 16, 2011

(86) PCT No.: PCT/FR2011/051377
§ 371 (c)(1),
(2), (4) Date: Dec. 17, 2012

(87) PCT Pub. No.: WO2011/157961
PCT Pub. Date: Dec. 22, 2011

(65) Prior Publication Data
US 2013/0114873 A1 May 9, 2013

Related U.S. Application Data

(60) Provisional application No. 61/355,377, filed on Jun. 16, 2010.

(30) Foreign Application Priority Data

Jun. 16, 2010 (FR) ...................................... 10 54785

(51) Int. Cl.
*G06K 9/00* (2006.01)
*G06K 9/62* (2006.01)
(Continued)

(52) U.S. Cl.
CPC .......... *G06K 9/6267* (2013.01); *A61B 19/5244* (2013.01); *G06K 9/4638* (2013.01);
(Continued)

(58) Field of Classification Search
CPC ..................... A61B 19/5244; A61B 2019/505; A61B 2019/5255; G06K 9/4638; G06K 2209/055; G06K 9/626; G06T 2207/30008; G06T 7/0083
USPC .................. 382/100, 128–132; 128/920, 922; 434/262, 245; 703/2, 6, 11; 606/1, 45, 606/130, 159; 600/101, 109, 112, 114, 600/117–118, 139, 145, 173, 420, 424, 434, 600/415–416, 562, 587
See application file for complete search history.

(56) References Cited

U.S. PATENT DOCUMENTS 7,599,539 B2 * 10/2009 Kunz et al. ..................... 382/128
7,831,079 B2 * 11/2010 Kunz et al. ..................... 382/128
(Continued)

FOREIGN PATENT DOCUMENTS

WO 2008014082 A2 1/2008

OTHER PUBLICATIONS

International Search Report and Written Opinion dated Aug. 15, 2011 for corresponding International Application No. PCT/FR2011/051377, filed Jun. 16, 2011.
(Continued)

*Primary Examiner* — Hadi Akhavannik
*Assistant Examiner* — Mehdi Rashidian
(74) *Attorney, Agent, or Firm* — David D. Brush; Westman, Champlin & Koehler, P.A.

(57) ABSTRACT

A method is provided for automatic identification of the contours of at least one portion of a predefined bone on the basis of a plurality of images representing parallel sections through a measurement volume including the portion of bone and which are obtained by a medical imaging technique. The method includes: a step of obtaining at least one shape of closed contour in at least one of the filtered images; a step of associating with each of the shapes a tag selected within a predefined bone-related nomenclature; a step of classifying the shapes so as to form at least one group of shapes delimiting a common volume isolated in space; a step of selecting the shapes of the group of target shapes.

16 Claims, 5 Drawing Sheets

(51) Int. Cl.
- *A61B 19/00* (2006.01)
- *G06K 9/46* (2006.01)
- *G06T 7/00* (2006.01)

(52) U.S. Cl.
CPC ............... *G06T 7/0083* (2013.01); *G06K 9/00* (2013.01); *A61B 2019/505* (2013.01); *A61B 2019/5255* (2013.01); *G06T 2207/30008* (2013.01); *G06K 2209/055* (2013.01)
USPC .......................................... 382/131; 382/128

(56) References Cited

U.S. PATENT DOCUMENTS

| 8,744,148 B2* | 6/2014 | Nord et al. | 382/128 |
|---|---|---|---|
| 2007/0249967 A1* | 10/2007 | Buly et al. | 600/595 |
| 2008/0025584 A1* | 1/2008 | Kunz et al. | 382/128 |
| 2009/0316975 A1* | 12/2009 | Kunz et al. | 382/131 |
| 2012/0051607 A1* | 3/2012 | Nord et al. | 382/128 |

OTHER PUBLICATIONS

Chien-Cheng Lee et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003, pp. 208-217, XP011100536.

Chien-Cheng Lee et al., "Recognizing Abdominal Organs in CT Images Using Contextual Neural Network and Fuzzy Rules", Engineering in Medicine and Biology Society, 2000. Proceedings of the 22nd Annual International Conference of the IEEE Jul. 23-28, 2000, Piscataway, NJ, USA, IEEE, vol. 3, Jul. 23, 2000, pp. 1745-1748, XP010530837.

Kobashi et al., "Knowledge-Based Organ Identification from CT Images", Pattern Recognition, Elsevier, GB, vol. 28, No. 4, Apr. 1, 1995, pp. 475-491, XP004013165.

Geoff Dougherty, "Digital Image Processing for Medical Applications", May 11, 2009, Cambridge University Press, XP002615721.

Tamez-Pena et al., "The Integration of Automatic Segmentation and Motion Tracking for 4D Reconstruction and Visualization of Musculoskeletal Structures" Biomedical Image Analysis, 1998. Proceedings. Workshop on Santa Barbara, CA, USA, Jun. 26-27, 1998, Los Alamitos, CA, USA, IEEE Comput. Soc. US, Jun. 26, 1998, pp. 154-163, XP010291418.

Nguyen et al., "A New Segmentation Method for MRI Images of the Shoulder Joint", Computer and Robot Vision, 2007. CRV '07. Fourth Canadian Conference on, IEEE, PI, May 1, 2007, pp. 329-338, XP031175821.

International Preliminary Report on Patentability and English translation of the Written Opinion dated Dec. 19, 2012, for corresponding International Application No. PCT/FR2011/051377, filed Jun. 16, 2011.

* cited by examiner

METHOD FOR AUTOMATICALLY IDENTIFYING THE CONTOURS OF A PREDEFINED BONE, DERIVED METHODS AND CORRESPONDING COMPUTER PROGRAM PRODUCTS

CROSS-REFERENCE TO RELATED APPLICATIONS

This Application is a Section 371 National Stage Application of International Application No. PCT/FR2011/051377, filed Jun. 16, 2011, which is incorporated by reference in its entirety and published as WO 2011/157961 on Dec. 22, 2011, not in English.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The field of the disclosure is that of medical imaging.

More specifically, the disclosure relates to a method for automatically identifying the contours of at least one portion of a predefined bone, a method for identifying the surface of a specific zone of a portion of bone and a computer program product for implementing these methods.

The disclosure is applied within the field of computer-assisted surgery, dedicated for example to shoulder bracing or arthroplasty. It also relates to a method for guiding a surgical tool, a method for simulating the fitting of a component of a prosthesis, and a computer program product for implementing these methods.

BACKGROUND OF THE DISCLOSURE

For a long time only two-dimensional images created by an X-ray unit were available to practitioners in order to make a diagnosis or prepare for a surgical operation in an osseous region.

For some years now, techniques for three-dimensional modeling of bone contours from images obtained by conventional medical imaging techniques, such as tomodensitometry, also known as scanning or MRI (magnetic resonance imaging) have been available to practitioners. However, in order to be implemented all of these known techniques require involvement on the part of the practitioner, to a greater or lesser extent, in particular in order to identify the bones to which the contours in each of the images correspond. This leads, fairly often, to an approximate assessment of the relative shape and position of the bones, which could lead to an inaccurate or erroneous diagnosis, or an unsuccessful orthopedic surgical operation with the aim, for example, of implanting a component of a prosthesis onto a bone.

It is noted that the rate of failure is slightly greater when the operation involves an articular region concealed by tissues and/or where access is limited. This is the case in particular with the shoulder joint, where surgery is made even trickier by the ligaments in the shoulder region.

There is thus a need for techniques which make it possible to assist or simulate the surgeon's movements, all the more so since the number of osseous or orthopedic surgical operations is expected to rise significantly in industrialized countries in the coming years.

Computer techniques which assist the surgical movement have certainly been proposed for surgery on the spinal column and for neurosurgery, these techniques being based on pre-operative X-ray images.

A drawback of these known techniques, called surgical navigation, is that they do not provide satisfactory results when applied to other types of surgery, in particular orthopedic surgery aimed at inserting a prosthetic implant.

A further drawback of these known surgical navigation techniques is that either the involvement of a support technician during the surgical operation is necessary, which is very costly, or the surgical team must undergo specific training in order to be able to carry out the tasks of the support technician for itself, which is difficult to implement in practice.

SUMMARY

An aspect of the disclosure relates to a method for automatically identifying the contours of at least one portion of a predefined bone from a plurality of images representing parallel sections of a measurement volume comprising said bone portion, said images being obtained by a medical imaging technique such as tomodensitometry or magnetic resonance imaging.

Within the scope of an embodiment of the invention the images from which said contours are extracted are preferably sections parallel to the transverse plane. The images may also be reconstructed sections parallel to the sagittal plane or frontal plane.

In accordance with an embodiment of the invention, such a method comprises:
  a step of filtering the images comprising a step of comparing, for each of said images, the intensity of at least one fundamental point of said image with a reference intensity, in such a way that a filtered image is obtained comprising said fundamental points of the image of which the density corresponds to that of an osseous tissue;
  a step of obtaining at least one shape of closed contour in at least one of the filtered images;
  a step of associating with each of the shapes a label selected within a predefined osseous nomenclature;
  a step of identifying said contours of said portion comprising:
    a step of classifying said shapes so as to form at least one group of shapes defining a common spatially isolated volume;
    a step of determining, from said shape groups, a target shape group for which said label corresponding to said bone is predominantly associated with said shapes in this group;
    a step of selecting shapes from said target shape group.

An embodiment of the invention thus suggests, in particular and in a novel manner, to automatically associate a label with each closed contour detected in an image of a series of parallel sections, by selecting said label within a predefined nomenclature so as to reproduce the contours of a given bone. These labels will make it possible to select a group of shapes belonging to the surface of a same isolated volume of space corresponding to the sought predefined bone. Indeed, the inventors have cleverly observed that it is suffice to determine the group of shapes within which the labels corresponding to the sought bone are predominant in order to access the contours of this bone.

An embodiment of the invention thus makes it possible to recognize the contours of a specific bone in a rapid and reliable manner, irrespective of the type of bone and irrespective of the measurement volume.

The implementation of an embodiment of the invention, which is also automatic, does not therefore require in any case the expertise of a practitioner in order to clear up any ambiguities, or the intervention of any other individual. It therefore does not suffer from any lacks of reproducibility.

In accordance with a specific embodiment of the invention, such an identification method further comprises a step of replacing the labels of the shapes of said target group which do not correspond to said predefined bone with said label which does correspond to said predefined bone.

An automatic correction of labeling anomalies is thus provided to homogenize the wording of labels associated with shapes related to the same bone, so as to simply call up the shapes of the bone sought by using the label which corresponds to it.

Preferably, said label belongs to the group comprising at least: long bone, flat bone, short bone, elongated bone, curved bone, arched bone, brittle bone, pneumatic bone, sesamoid bone, examination table.

In accordance with an advantageous aspect of an embodiment of the invention, said step of association comprises, for each of said shapes, the following steps in this order:
  a step of comparing an n-uplet of dimensionless data with at least one predefined n-uplet, n being greater than or equal to 2, said data belonging to the group comprising at least the elongation, density, the encompassing rectangle and the normalized moments of inertia of said shape of closed contour;
  if said set of n values is substantially similar to one of said predefined n-uplets, a step of assignment to said shape of a label attached to said predefined n-uplet.

These steps of comparison and conditional assignment thus make it possible, in general, to detect ribs, an examination table or epiphyseal portions in an assured manner.

It should be noted that the predefined n-uplet(s) is/are preferably extracted from a database formed, for each type of bone, from anatomical information on a large patient population, this database being validated by a medical expert.

Advantageously, said step of association comprises a step of assigning to said shape a label attached to a predefined normalized invariant vector selected from a plurality of predefined normalized invariant vectors, thus minimizing the distance from a normalized invariant vector formed of a predetermined number of normalized coefficients representative of the coordinates of said contour in the Fourier space.

The Fourier descriptors of each shape are thus compared to the vectors of a reference shape dictionary, which makes it possible to distinguish long bones, short bones or other bones, such as elongated bones, curved bones, arched bones, brittle bones, pneumatic bone or sesamoid bones.

Advantageously, said predetermined number of coefficients is greater than or equal to 8, and is preferably equal to 32.

Said step of obtaining at least one shape of closed contour advantageously comprises a step of applying at least one morphological filter to said filtered image.

This makes it possible to eliminate the noise in the images and to preserve merely the shapes of which the contour is of a size which is sufficient to correspond to the contour of a bone.

In a specific embodiment of the invention said predefined bone is a scapula or humerus.

An embodiment of the invention also relates to a method for automatically identifying the surface of at least one specific zone, such as a protrusion, a cavity or a substantially planar zone, over a portion of a predefined bone of which the contours have been obtained in accordance with any one of the above-described methods for automatically identifying the contours of at least one portion of a predefined bone.

Such a method for automatically identifying the surface of at least one specific zone comprises:
  a step of obtaining the three-dimensional position of at least one specific point of said surface of said portion of a predefined bone from said contours;
  a step of identifying said surface of said specific zone in a segment of a sphere centered around said point, said segment of a sphere having a predefined radius and thickness and being a function of said point.

Owing to an embodiment of the invention, a technique which makes it possible to automatically identify the surface of a zone of a bone is thus proposed for the first time. This technique has considerable benefits, both independently in order to optimize the position of implantation of a pre-existing prosthetic component in a specific zone of a bone, and so as to produce a prosthetic component which is especially adapted to said specific zone.

This original technique is based on the identification of the "signature shape" of the sought zone, or in other words the distance between this zone and one or more specific points of the bone, which are easily detectable, such as the end of a toe.

This specific zone may, for example, be the acromion, the glenoid surface, or the coracoid process in the case of a scapula.

An embodiment of the invention also relates to a method for automatically determining initial parameters of a transfer matrix between a first coordinate system associated with at least one portion of a bone of a patient and a second coordinate system associated with the contours of said portion of bone identified over a plurality of images obtained by a medical imaging technique capturing sections of a measurement volume comprising said portion of bone.

According to an embodiment of the invention, this method for automatically determining the initial parameters of a transfer matrix comprises:
  a step of automatically identifying the surface of a specific zone in said images comprising the steps of the above-described method for automatically determining the surface of at least one specific zone over the surface of a bone;
  a step of determining the barycenter of said specific zone and of the vector normal to the median plane of said surface of said specific zone oriented towards the outside;
  a step of obtaining registration parameters, resulting from the coincidence of said barycenter and said normal vector, determined with the barycenter of said specific zone digitized over said portion of bone and a vector normal to the median plane of the surface of said digitized specific zone, oriented towards the outside;
  a step of forming said initial parameters from said registration parameters.

A robust, initial transfer matrix is thus obtained which makes it possible to precisely register the first coordinate system associated with the patient and the second coordinate system associated with the modeling of the contours of the bone by applying to said matrix algorithms, which are known per se, for minimizing distances. Any risk of divergence to unsuitable local minima is eliminated.

This initial transfer matrix is also obtained automatically, or in other words without the involvement of a practitioner. In contrast to known techniques, it is neither necessary to visually locate three points of the second coordinate system in the X-ray images, nor to digitize these same three points on the bone of the patient. The practitioner must merely first digitize the surface of the selected specific zone, which is quick and does not need to be precise.

It should be noted that, within the scope of an embodiment of the invention, the terms "digitization" are understood to mean any technique which makes it possible to collect information regarding the three-dimensional position of a point or surface of an object or a human being. For example, it may be an optical digitization technique carried out with the aid of a laser, a digitization technique carried out with the aid of an echographical probe, or a three-dimensional measurement technique carried out with the aid of 3D sensors.

An embodiment of the invention also relates to a method for simulating of the positioning of an element of a prosthesis in a specific zone of a portion of a predefined bone, comprising:
- a step of automatically identifying the surface of said specific zone in images of said portion of a predefined bone obtained by a medical imaging technique, comprising the steps of the above-described method for automatically identifying the surface of at least one specific zone over a portion of a bone;
- a step of determining a first piece of information comprising the reference plane of said surface and/or the angle of version and/or the angle of inclination associated with said surface;
- a step of determining a second piece of information which is representative of the osseous capital associated with said surface, said information being determined from the data regarding said surface and the data regarding the contours of said portion of bone obtained in accordance with any one of the above-described methods for automatically identifying the contours of at least one portion of a predefined bone;
- a step of reproducing said first and second pieces of information compared with at least one geometrical parameter of the element of the prosthesis.

As a result of this method, the practitioner is thus automatically provided with information regarding the geometry of the zone for implantation of the prosthetic element, and also with information regarding the osseous capital in this zone.

An embodiment of the invention also relates to a computer program product which can be downloaded from a communications network and/or recorded on a support which can be read by the computer and/or run by a processor, said computer program product comprising program code instructions for carrying out the steps of any one of the above-described methods for automatically identifying the contours of at least one portion of a predefined bone and/or the steps of a method, as described above, for automatically identifying at least one specific zone over a portion of a predefined bone and/or the steps of the method, described above, for automatically determining the initial parameters of a transfer matrix and/or the steps of the method, as described above, for simulating an element of a prosthesis in a specific zone of a portion of a predefined bone, when said program is run by a computer.

A surgical method for implanting an element of a prosthesis in a specific zone of a portion of a bone of a patient, for example a bone of a joint and in particular the shoulder joint, is also defined here and comprises:
- a step of obtaining, by a medical imaging technique, a plurality of images representing parallel sections of a measurement volume comprising said portion of bone;
- a step of automatically identifying the surface of said specific zone comprising the steps of the above-described method according to the invention for automatically identifying the surface of at least one specific zone over a portion of a bone;
- a step of combining spatial location means with said portion of bone, said means associating a first coordinate system with said portion of bone;
- a step of digitizing said specific zone;
- a step of automatically registering said first coordinate system with a second coordinate system associated with the contours of said portion of bone identified from said plurality of images by implementing any one of the above-described methods according to an embodiment of the invention for automatically identifying the contours of at least one portion of a predefined bone from a plurality of images, comprising the steps of the above-described method according to the invention for automatically determining the initial parameters of a transfer matrix;
- a step of combining location means with said prosthetic element so as to provide the position and orientation of said prosthetic element relative to said first coordinate system;
- a step of implanting, by a practitioner, said prosthetic element in said specific zone within a spatial configuration determined at least from the representation of the position and contours of said prosthetic element and of at least said identified surface of said specific zone in said first coordinate system.

A method for guiding a surgical tool for removing at least part of a portion of a bone of patient is also described here and comprises:
- a step of obtaining, by a medical imaging technique, a plurality of images representing parallel sections of a measurement volume comprising said portion of bone;
- a step of automatically identifying the contours of said portion of bone from said plurality of images, comprising the steps of any one of the above-described methods for automatically identifying the contours of at least one portion of a predefined bone from a plurality of images;
- a step of connecting spatial location means to said portion of bone, said means associating a first coordinate system with said portion of bone;
- a step of digitizing said specific zone;
- a step of automatically registering said first coordinate system with a second coordinate system associated with said contours of said portion of bone identified from said plurality of images by implementing any one of the above-described methods for automatically identifying the contours of at least one portion of a predefined bone from a plurality of images, comprising the steps of the above-described method for automatically determining the initial parameters of a transfer matrix;
- a step of connecting location means to said surgical tool so as to provide the position and orientation of said surgical tool relative to said first coordinate system;
- a step of guiding said tool, at least from the representation of the position and contours of said tool and of said portion of bone in said first coordinate system.

BRIEF DESCRIPTION OF THE DRAWINGS

Further features and advantages will become clearer upon reading the description below of an embodiment of the invention, which is given merely by way of non-limiting example, and from the accompanying drawings, in which.

DETAILED DESCRIPTION OF ILLUSTRATIVE EMBODIMENTS OF THE INVENTION

1. Summary of an Exemplary Principle of an Embodiment of the Invention

As already indicated, the principal of an embodiment of the invention is based, in particular, on the implementation of systematic labeling of osseous shapes detected automatically in images obtained by scanner or MRI examination, using a suitable osseous nomenclature defined in advance and formed of a limited number of different generic labels. This labeling then makes it possible to automatically identify the solid volume corresponding to the sought bone.

An embodiment of the invention also makes it possible to re-label some shapes if the label which has been attributed to this shape is different to that associated with the majority of shapes relating to the same bone as that to which said shape is related.

2. Embodiment of the Invention

Figure 1:
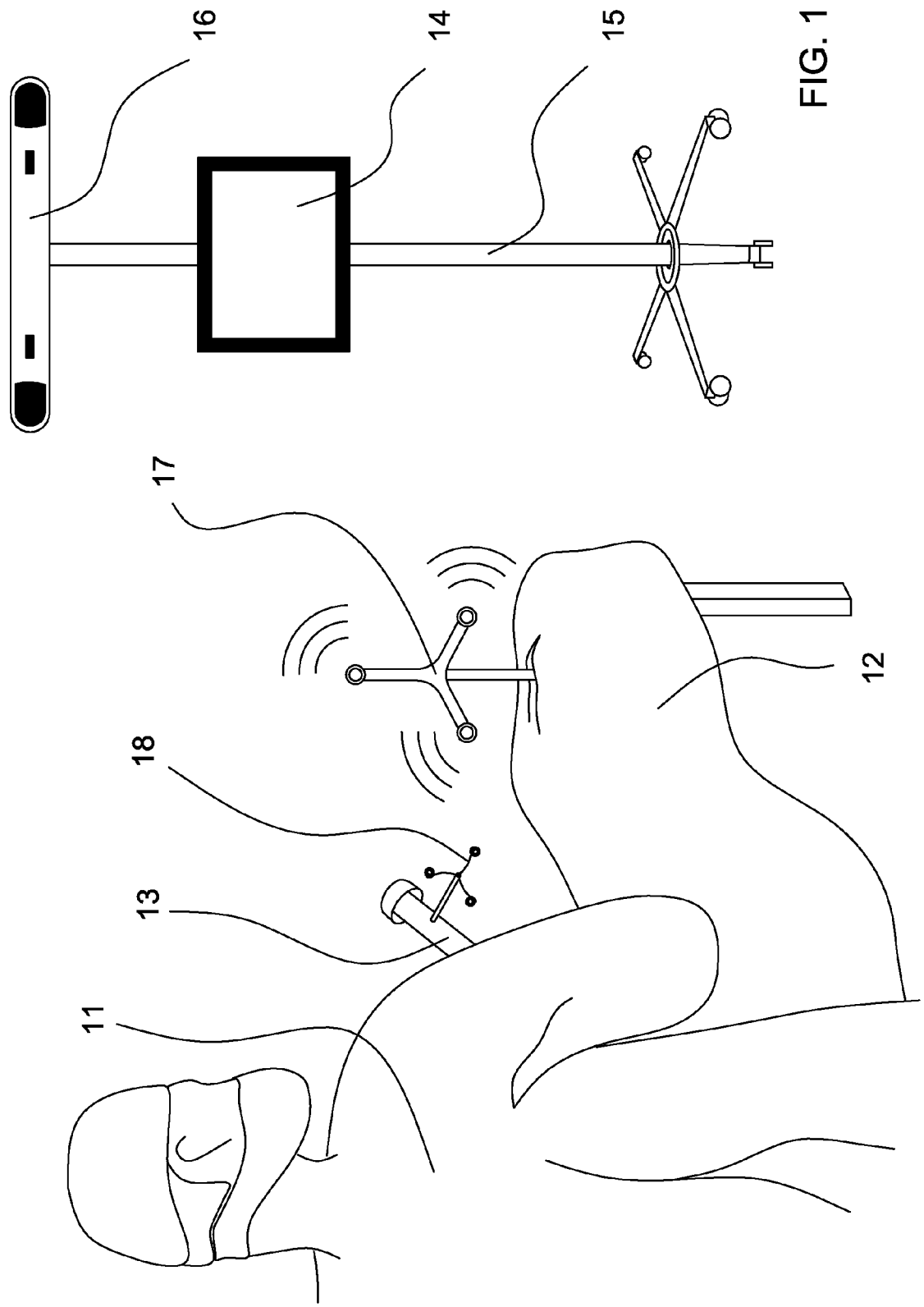
FIG. 1 shows a surgeon, during a prosthetic surgical operation on the shoulder, using a navigation station accommodating a software application for implementing an embodiment of methods according to an embodiment of the invention.

FIG. 1 shows a surgeon 11 preparing to implant a glenoid component of a shoulder prosthesis (not shown in FIG. 1) in the glenoid surface of the right-hand scapula of a patient 12 over the course of an orthopedic surgical operation on the shoulder. Whilst displacing the glenoid prosthetic component at the end of the sleeve 13, said surgeon 11 can observe, in real time, the position of said component relative to the surface of the scapula on the screen 14 of a navigation station 15 equipped with an optical localizer 16.

Figure 2:
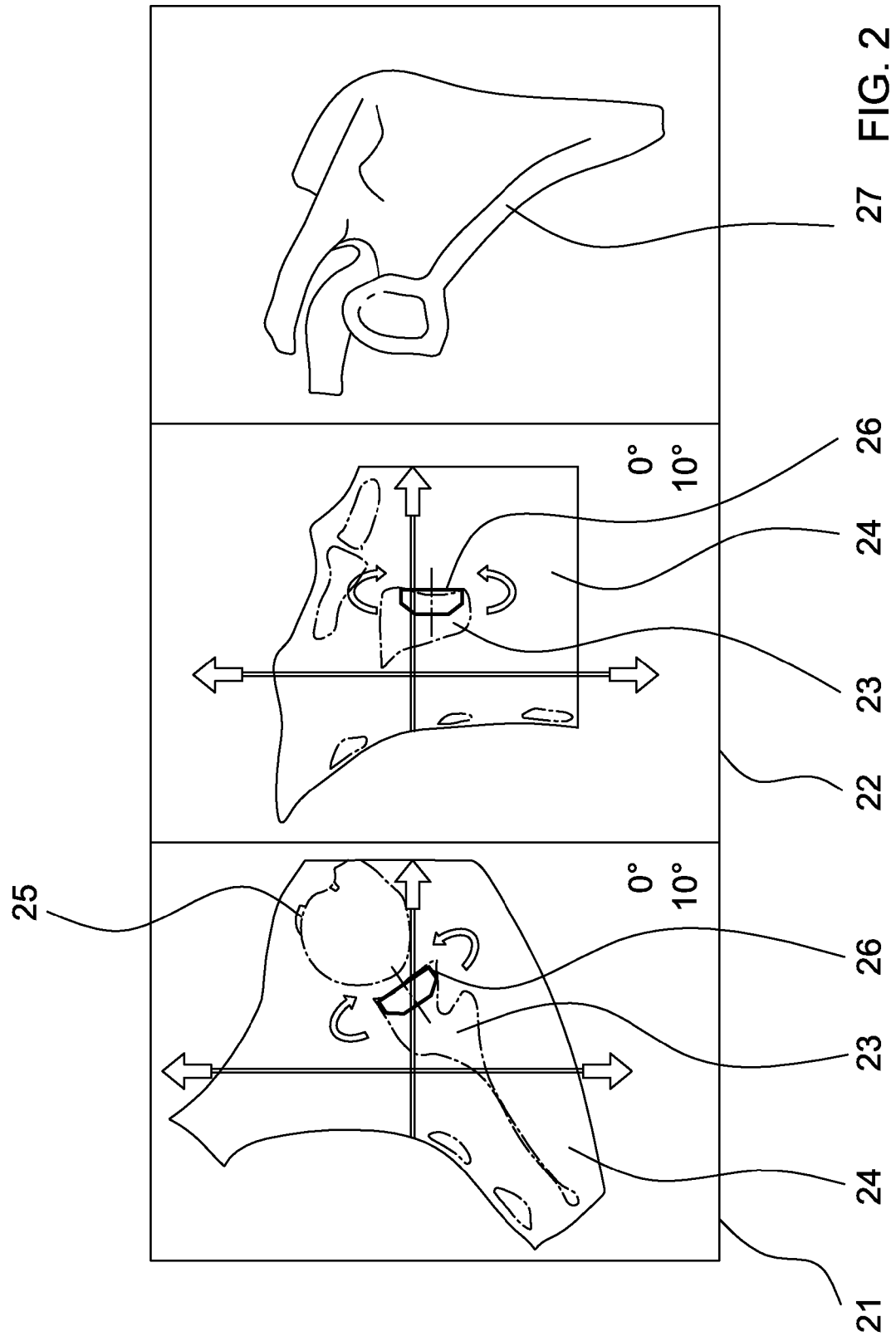
FIG. 2 shows an image displayed on the screen of the navigation station shown in FIG. 1.

FIG. 2 shows a detail of three windows displayed on the screen 14. The same 2D section of the region of the shoulder joint along a transverse plane can be seen in the left (frame 21) and centre (frame 22) windows, in which the contour of the glenoid surface 23, and more generally the surface 24 of the scapula, the contour of the humeral head 25 and a contour of the glenoid prosthetic component 26 are highlighted. Within the frame 21, the contour 26 is shown in its actual position relative to the scapula. The frame 22 allows the surgeon to visualize an optimal theoretical position of implantation of the glenoid prosthetic component.

In addition, the values of the angles of retroversion and inclination, at 0 and 10° respectively, are displayed on the screen 14. Further information such as the reference plane of the scapula, the reference plane of the glenoid surface, the angle of version of the glenoid surface and the osseous capital of the glenoid bone can also be accessed automatically by implementing an embodiment of the invention. The reproduction of this information compared to the geometric contour 26 of the glenoid component has enabled the surgeon to optimize the shape of said prosthetic element and to simulate the positioning of said element before the operation.

The contours 27 of the scapula are shown in 3D on the right-hand side in FIG. 2. These contours were modeled previously, by a first software application, in a pre-operative phase using the method according to an embodiment of the invention for automatically identifying contours of a portion of bone, this method being parameterized for the shoulder region. These contours were obtained from approximately 100 images of 2D cross-sections of a measurement volume centered over the shoulder joint, after the patient had visited a radiology department in order to undergo a scanning process. The 2D sections have a resolution substantially equal to 0.5 mm in this embodiment of the invention.

Figure 3:
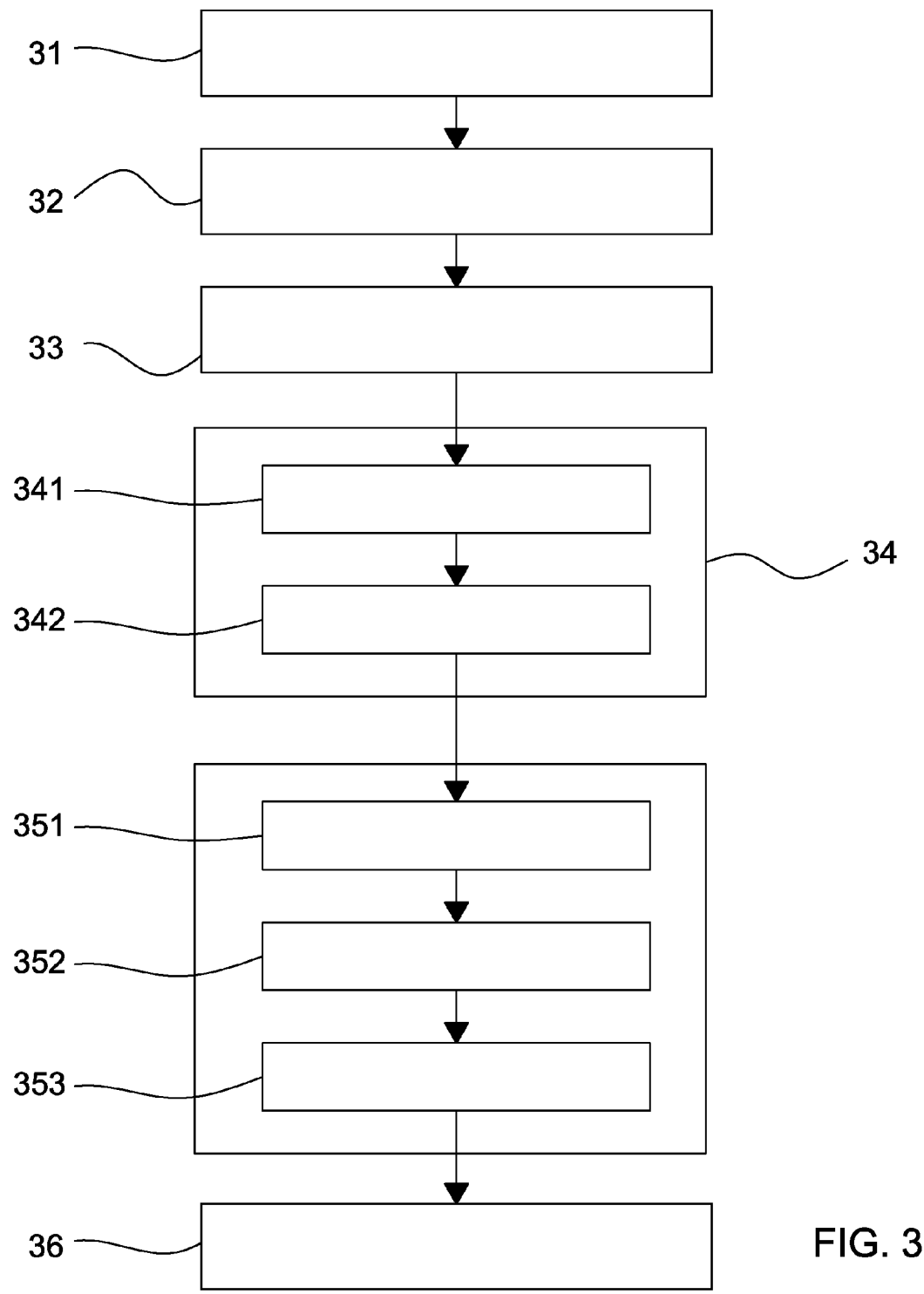
FIG. 3 shows, in the form of a block diagram, the steps of an embodiment of the method according to an embodiment of the invention for automatically identifying the contours of a scapula.
Figures 4A, 4B, 4C:
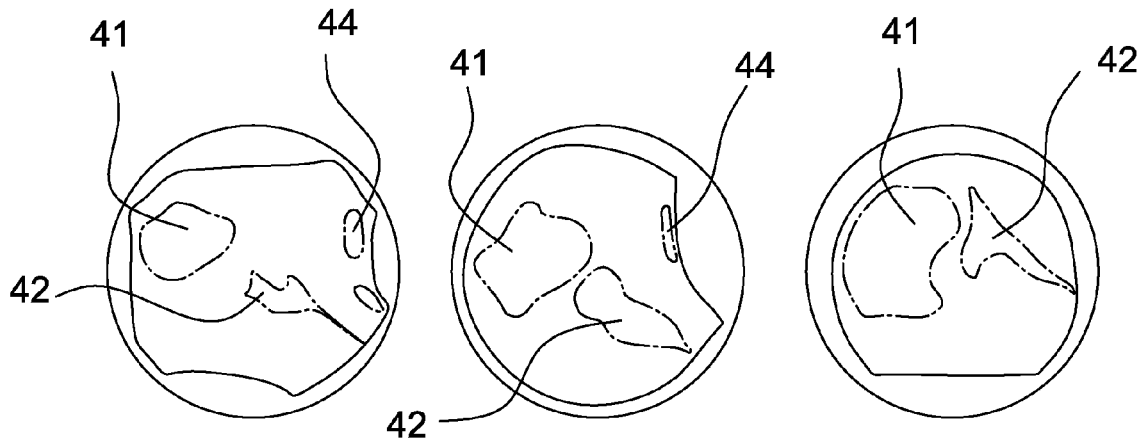
FIGS. 4A to 4E show images of different cross-sections, in which labeled shapes are located.
Figures 4D, 4E:
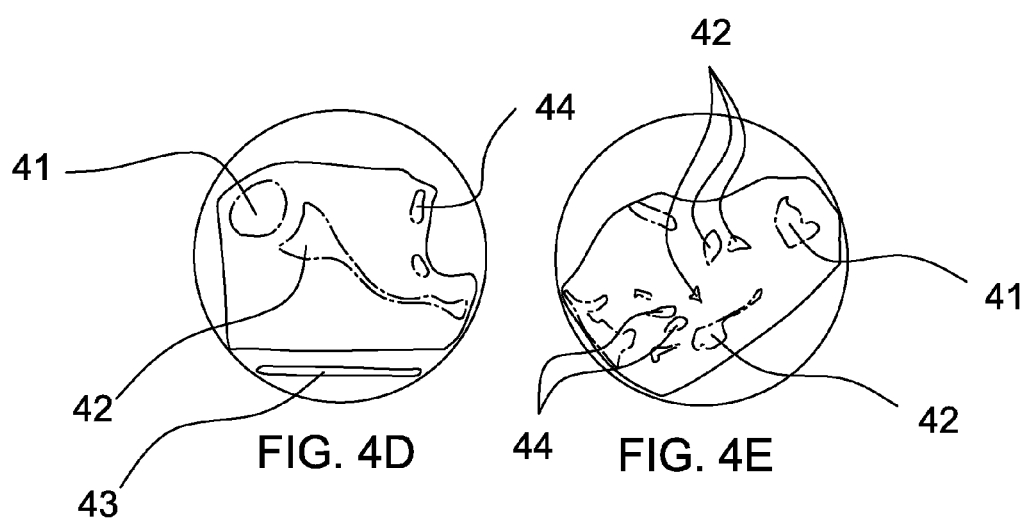

FIG. 3 shows, in the form of a block diagram, the steps of an embodiment of the method for automatically identifying contours, this method being implemented so as to obtain the contours 26.

In a first step 31 the 2D sectional images are filtered so as to conserve merely the fundamental points of the image of which the density corresponds to that of an osseous tissue. To this end, the intensity of each point of the image for example, expressed for example in Hounsfield units, is compared to a reference intensity which is fixed in this embodiment of the invention at 250 Hounsfield, and the points of the image of which the intensity is less than this reference intensity are disregarded. In a variation of this embodiment, it may also be envisaged to disregard the points of the image of which the intensity is greater than 300 Hounsfield, these points being characteristic of bodies of which the intensity is greater than the known maximum osseous density.

In a second step 32, morphological filters of known formulation are applied to the filtered images, with the aim of detecting shapes of closed contour, or related components, of considerable size within each image. This procedure of segmentation makes it possible to delete the related components of reduced size from the image.

The inside of the closed contours is also filled in a following step 33, thus removing from the image the related components which resemble inner cortical bone.

A label selected from a predefined osseous nomenclature is then associated with each of the shapes of closed contour remaining in the image in a step 34. This nomenclature groups the following labels in this embodiment of the invention dedicated to identification of shoulder bone: "long bone", "flat bone", "other bone" and "examination table".

During the step 34, the values of three dimensionless geometric parameters specific to each shape and forming a triplet are compared one by one in a preliminary step 341 to the corresponding predefined values of each reference triplet of a database.

This pre-established database was formed from anatomical information obtained on a large population of patients. It has a correlation table which corresponds to a predefined label of the osseous nomenclature to each reference triplet.

If the triplet specific to a shape is substantially similar to a reference triplet, or in other words if each of the parameters differs merely by a few percent from the values of one of the reference triplets, the label attached to this reference triplet, for example the long bone label, is assigned to this shape.

The geometric parameters retained in this embodiment are:
elongation, which is defined as the ratio of the diameter of the inscribed circle of the contour to the diameter of the circumscribed circle of the contour of the shape;
the encompassing rectangle, which is defined as the ratio of the length to the width of a circumscribed rectangle of which the edges are tangent to the contours of the shape;
compactedness, which is defined as the ratio of the length of the contour of the shape to the inner surface of the contour.

In variations of this embodiment, two, four, five or more dimensionless geometric parameters specific to each shape can be compared to predefined pairs, quadruplets or quintuplets collected in the reference database, and/or a normalized moment of inertia of the shape may constitute one of these geometric parameters, for example.

The inventors have noted that this step 341 is often sufficient to identify shapes of the examination table, owing to their considerable elongations, and ribs. In this embodiment the label "other bone" is attributed to shapes recognized as those of ribs.

In a following step 342, a label will be automatically assigned to each of the shapes still without a label at the end of step 341.

During this step 342, the first 32 normalized invariant Fourier descriptors are determined for each of the unlabeled shapes from their contour, or in other words the first 32 coefficients of the Fourier transform from their contour, normalized so as to make them independent of scale factors and invariant to rotation and translation. It is noted that 32 Fourier descriptors are generally sufficient to account for the complexity of the contours of a long bone, for example.

In variations, it may be envisaged to determine 8, 16 or 64 first Fourier descriptors of these contours depending on the complexity of the contours to be processed.

A normalized invariant vector is then formed from these 32 first descriptors, and a shape recognition process is then applied to this vector. More specifically, the distance between this vector and each of the normalized invariant vectors from a library of pre-established bone contour shapes is evaluated, and the label attached to the vector from the library minimizing this distance, within the meaning of the Euclidean standard for example, is assigned to the shape processed.

FIGS. 4A to 4E show the results of label association with shapes of closed contour in different parallel sections obtained at the end of step 34. In these figures it is possible to distinguish between shapes 41 associated with the "long bone" label and corresponding to the humerus, shapes 42 associated with the "flat bone" label and corresponding to the scapula, shapes 43 associated with the "examination table" label, and shapes 44 associated with the "other bone" label and comprising rib sections.

In a last step 35, the contours of the scapula are identified by classifying the shapes by shape group (step 351), for example by applying a method of hierarchical or stochastic classification which is known per se. More specifically, the shapes belonging to the surface of a same spatially isolated three-dimensional volume are sorted by group, or in other words solid 3D volumes are reconstructed from the shapes obtained from step 32.

In this specific embodiment of the invention, the following approach is adopted in practice in order to classify the shapes:

In the case of two images corresponding to adjacent parallel layers, shapes of which the contours are substantially superposed when these images are projected one onto the other are sought. In particular, it is checked as to whether their centers of gravity and their contours substantially coincide, for example owing to their proximity or the fact that they cross a number of times, which makes it possible to reconstruct, step-by-step, each of the solid volumes, i.e. the bones of measurement volume obtained by CT scan.

In a step 352 the group of shapes is determined which is known as the target shape group and for which the "flat bone" label, corresponding to the scapula, is predominantly associated with the shapes of the group. It should be noted that, within the scope of an embodiment of the invention, the idea of "predominance" is understood within a wide acceptance. For example, it may be an estimation based at least in part on a statistical criterion.

The contours of the scapula, which are the contours of the target shape group and have been selected (step 353), have thus been identified automatically.

A further step 36 is also provided to take into account any labeling errors within the shapes of the target shape group. More specifically, the labels of shapes in this group which are different to "flat bone" are replaced with the "flat bone" label corresponding to the scapula.

The data regarding the identified contours of the scapula were then processed, during the pre-operative phase, by a second software application which makes it possible to automatically extract a three-dimensional representation of the glenoid surface from its "signature shape".

Figure 5:
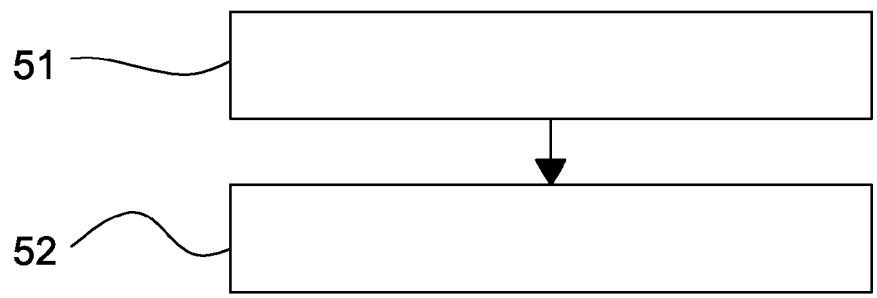
FIG. 5 is a block diagram showing the steps of the method for automatically identifying the glenoid surface according to an embodiment of the invention.

The steps which make it possible to identify this surface are detailed in the form of a block diagram in FIG. 5.

In a step 51 the three-dimensional position of a specific anatomical point of the scapula close to the glenoid surface is located on the basis of the numeric model of the scapula reconstructed from its contours.

In a step 52 the glenoid surface is sought within a segment of a sphere centered about this point, said segment of a sphere having a predefined radius and thickness as a function of the distance generally established between said specific point and the glenoid surface, and as a function of a theoretical estimation of the size of the glenoid surface.

The median plane within the meaning of least squares, the angle of version and the angle of inclination of the glenoid bone are then determined by a routine of normal calculation.

A similar procedure is used to obtain a 3D numerical modeling of the surface of the acromion and the surface of the coracoid process.

Before introducing the component 26 into the incision with the aim of implanting it in a predetermined spatial configuration, the surgeon has carried out the following tasks, which require merely a few minutes, in order to obtain the image of FIG. 2:

he has connected, with the aid of a clip, a tripod carrying a rigid body 17, or reference "tracker" including markers which passively reflect the infrared radiation towards the optical localizer 16 so as to associate a spatial coordinate system with the scapula. It is noted that, in a variant, this tracker may be an active tracker equipped with infrared diodes, or else an electromagnetic tracker if a magnetic localizer is used;

he has felt the glenoid surface so as to make it possible to automatically calculate an initial transfer matrix associated with the numerical modeling of the scapula 26;

as an auxiliary measure, he has felt the surface of the acromion and the surface of the coracoid process in order to refine the parameters of this initial transfer matrix.

A tripod 18, carrying a rigid body, is also connected on the sleeve 13, which makes it possible to locate the spatial position of the prosthetic component 26. The position relative to the component 26 relative to the tripod 18 has been obtained by a known calibration technique.

The registration between the spatial coordinate system of the patient's scapula, also referred to hereinafter as the first coordinate system, and a second coordinate system associated with the numerical modeling of the scapula is carried out automatically by a software application, making it possible to estimate a transfer matrix between these two coordinate systems.

Figure 6:
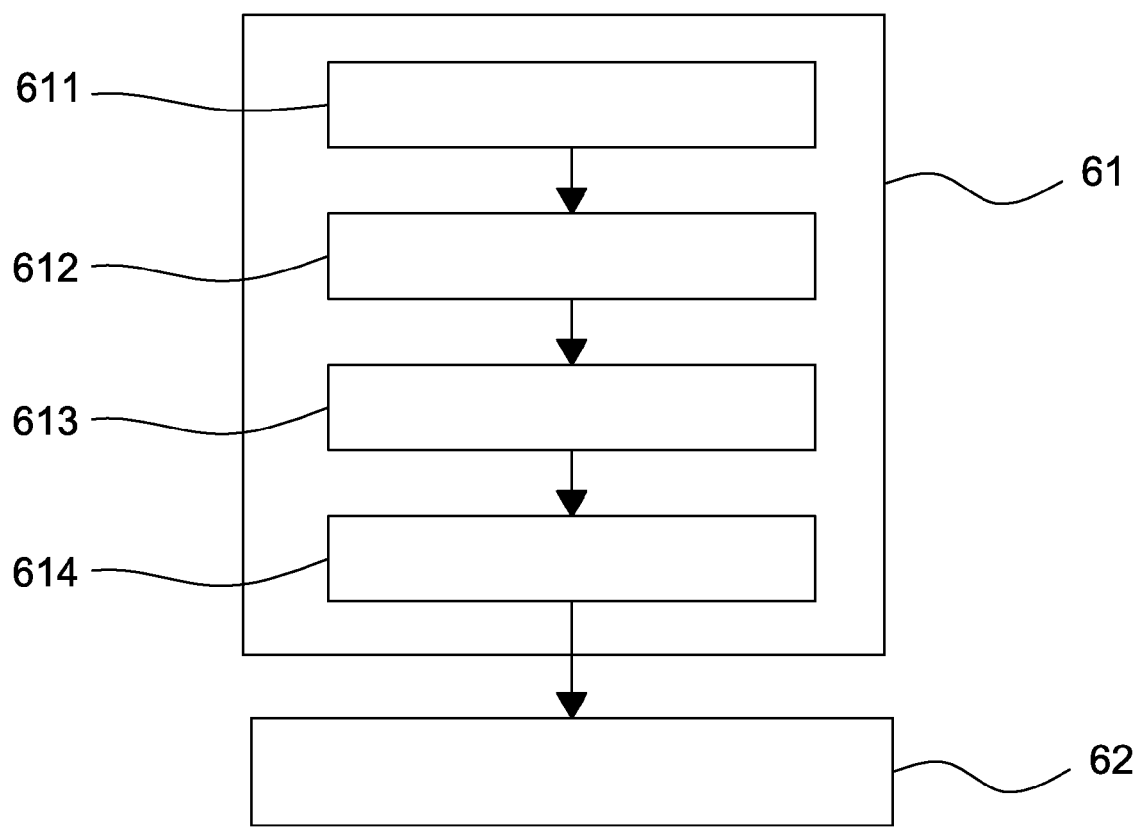
FIG. 6 shows, in a block diagram, the steps of an embodiment of the method according to the invention for automatically determining the initial parameters of a transfer matrix.

As can be seen in the block diagram of FIG. 6, the parameters of this transfer matrix are determined in two phases which are represented by dotted lines in FIG. 6.

The initial parameters, which make it possible to result in this matrix, are determined in a first phase 61.

In a second phase 62 a known iterative registration algorithm is applied to a matrix formed from said initial parameters, also known loosely as initial transfer matrix, which makes it possible to obtain the parameters of a refined transfer matrix making it possible to minimize the distance between the surface of the felt zones of the scapula and the numerical modeling of this surface obtained in accordance with the method for identifying the surface shown with reference to FIG. 5.

During the phase 61 the barycenter of the 3D numerical modeling of the glenoid surface, identified via steps 51 and 52, is calculated in a step 611. The vector normal to the median plane of this modeled glenoid surface and oriented towards the outside of the scapula is also determined in this step 611. This calculation is carried out by using a robust approximation within the meaning of least squares of the points of the surface by a plane with the aim of minimizing the sum of the squares of the distances between the points of the surface and the sought plane whilst eliminating the deviant data of which the distance to the plane is greater than three times the variance of the distances for all the points.

In a following step 612, the registration parameters making it possible to coincide respectively the coordinates of the barycenter obtained in step 611 with the coordinates of the barycenter of the glenoid surface digitized by probing, and the coordinates of the vector obtained in step 611 with those of the vector normal to the median plane of the digitized glenoid surface, of known orientation thanks to sensors, are evaluated. The rotation around this normal vector remains undetermined at this moment.

The registration parameters are then translated into initial parameters of the transfer matrix in a step 613.

These initial parameters are refined in a following step 614 by minimizing the distance between the theoretical surfaces of the acromion and the coracoid process, which are calculated automatically from the scanner images, and the coordinates resulting from the digitization by probing of the surface of the acromion and the surface of the coracoid process by carrying out rotations about the axis defined by the vector normal to the median plane of the glenoid surface so as to minimize the distance between the probed points and the modeled surfaces. To this end the Levenberg-Marquardt algorithm can be applied, for example.

Figure 7:
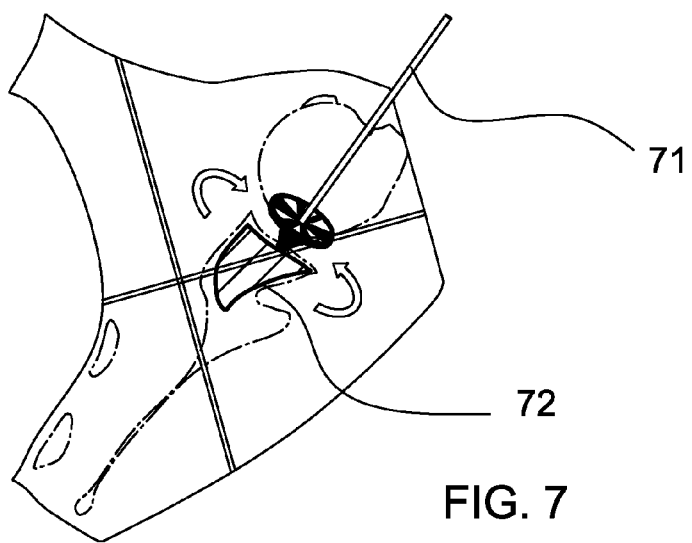
FIG. 7 is a view of an interface for guiding the movement of a surgeon manipulating a surgical tool.

3. Further Optional Features and Advantages of an Embodiment of the Invention In variations of the embodiment of the invention detailed above, the surgeon's movement can also be guided whilst he manipulates a surgical milling tool, a surgical bone drill or any other surgical tool, by displaying on the screen 14 the position and angle of the tool 71, which he is holding in his hand, relative to the drilled bone 72, for example in the manner shown in FIG. 7. This guidance, which is enabled by the guiding method according to an embodiment of the invention, requires connection of a coordinate system to the tool. It makes it possible to control the movement of the surgeon during an intricate operation and for example during shoulder arthroplasty.

In a further variation it may be envisaged, without departing from the scope of the invention, that the nomenclature can also include at least one of the following labels: short bone, elongated bone, curved bone, arched bone, brittle bone, pneumatic bone, sesamoid bone.

An embodiment of the invention provides a technique for identifying the contours of a portion of a predefined bone from images obtained by medical imaging techniques which are known per se, which technique functions automatically, or in other words does not require human intervention.

An embodiment of the invention also provides such a technique which is simple and effective.

An embodiment of the invention provides such a technique which is reliable.

An embodiment of the invention provides such a technique which can be used under surgical conditions by providing, in particular, the contours of a bone within an acceptable period of time.

An embodiment of the invention provides such a technique which can make it possible to automatically manage losses in contour or fusion between two different osseous regions without making substantial modifications to the implementation of this technique.

At least one specific embodiment of the invention further provides information which is representative of the osseous capital of a region of a predefined bone.

An embodiment of the invention facilitates and makes robust the registration of the identified contours with a surgical coordinate system, as is necessary in a surgical navigation system.

Although the present disclosure has been described with reference to one or more examples, workers skilled in the art will recognize that changes may be made in form and detail without departing from the scope of the disclosure and/or the appended claims.

The invention claimed is:

1. A method for automatically identifying the contours of at least one portion of a predefined bone from a plurality of images representing parallel sections of a measurement volume comprising said bone portion, said images being obtained by a medical imaging technique, wherein the method comprises:
   a step of filtering the images with a processor, comprising a step of comparing, for each of said images, the intensity of at least one fundamental point of said image with a reference intensity, in such a way that a filtered image is obtained comprising said fundamental points of the image of which a density corresponds to that of an osseous tissue;
   a step of obtaining at least one closed contour shape in at least one of the filtered images;
   a step of associating each of the shapes of a label selected with a predefined osseous nomenclature;
   a step of identifying said contours of said portion of bone comprising:
      a step of classifying said shapes so as to form at least one group of shapes defining a common spatially isolated volume;

a step of determining, from said shape groups, a target shape group for which said label corresponding to said bone is associated, predominantly, with said shapes of this group;

a step of selecting shapes from said target shape group.

2. The identification method according to claim 1, wherein the method further comprises a step of replacing the labels of the shapes of said target group which do not correspond to said predefined bone with said label which does correspond to said predefined bone.

3. The identification method according to claim 1, wherein said label belongs to the group consisting of:
long bone;
flat bone;
short bone;
elongated bone;
curved bone;
arched bone;
brittle bone;
pneumatic bone;
sesamoid bone;
examination table.

4. The identification method according to claim 1, wherein said step of association comprises, for each of said shapes, the following steps in this order:
a step of comparing an n-uplet of dimensionless data with at least one predefined n-uplet, n being greater than or equal to 2, said data belonging to the group comprising at least elongation, density, encompassing rectangle and normalized moments of inertia of said shape of closed contour;
if said set of n values is substantially similar to one of said predefined n-uplets, a step of assigning to said shape of a label attached to said predefined n-uplet.

5. The identification method according to claim 1, wherein said step of association comprises a step of assigning to said shape a label attached to a predefined normalized invariant vector selected from a plurality of predefined normalized invariant vectors, thus minimizing distance from a normalized invariant vector formed of a predetermined number of normalized coefficients representative of the coordinates of said contour in Fourier space.

6. The identification method according to claim 5, wherein said predetermined number of coefficients is greater than or equal to 8.

7. The identification method according to claim 1, wherein said step of obtaining at least one shape of closed contour advantageously comprises a step of applying at least one morphological filter to said filtered image.

8. The identification method according to claim 1, wherein said predefined bone is a scapula or a humerus.

9. The identification method according to claim 1, further comprising automatically identifying a surface of at least one specific zone over a portion of the predefined bone of which the contours have been obtained, wherein identifying a surface comprises:
a step of obtaining a three-dimensional position of at least one specific point of said surface of said portion of the predefined bone from said contours; and
a step of identifying said surface of said specific zone in a segment of a sphere centered around said point, said segment of a sphere having a predefined radius and thickness and being a function of said point.

10. The identification method according to claim 9, wherein said predefined bone is a scapula and said specific zone belongs to the group consisting of:

acromion;
glenoid surface;
coracoid process.

11. The identification method according to claim 9, further comprising automatically determining initial parameters of a transfer matrix between a first coordinate system associated with the portion of the bone of a patient and a second coordinate system associated with the contours of said portion of bone identified in the plurality of images obtained by the medical imaging technique illustrating sections of a measurement volume comprising said portion of bone, automatically determining the initial parameters comprises:
the step of automatically identifying the surface of the specific zone in said images;
a step of determining a barycenter of said specific zone and of a vector normal to a median plane of said surface of said specific zone oriented towards the outside;
a step of obtaining registration parameters resulting from coincidence of said barycenter and said normal vector determined with the barycenter of said specific zone digitized over said portion of bone and the vector normal to the median plane of the surface of said digitized specific zone, oriented towards the outside; and
a step of forming said initial parameters from said registration parameters.

12. The identification method according to claim 9, further comprising:
simulating a positioning of an element of a prosthesis in the specific zone of the at least one portion of the predefined bone, comprising:
a step of determining a first piece of information comprising at least one of a reference plane of said surface, an angle of version, or an angle of inclination associated with said surface;
a step of determining a second piece of information which is representative of osseous capital associated with said surface, said information being determined from data regarding said surface and data regarding contours of said portion of bone; and
a step of reproducing said first and second pieces of information compared to at least one geometrical parameter of the element of the prosthesis.

13. A non-transitory computer-readable medium comprising a computer program product wherein said computer program product comprises program code instructions for carrying out steps of a method for automatically identifying the contours of at least one portion of a predefined bone from a plurality of images representing parallel sections of a measurement volume comprising said bone portion, said images being obtained by a medical imaging technique, when said instructions are executed by the processor, wherein the instructions comprise:
instructions that configure the processor to filter the images, comprising a step of comparing, for each of said images, intensity of at least one fundamental point of said image with a reference intensity, in such a way that a filtered image is obtained comprising said fundamental points of the image of which a density corresponds to that of an osseous tissue;
instructions that configure the processor to obtain at least one closed contour shape in at least one of the filtered images;
instructions that configure the processor to combine each of the shapes of a label selected within a predefined osseous nomenclature; and
instructions that configure the processor to identify said contours of said portion of bone, comprising:

a step of classifying said shapes so as to form at least one group of shapes defining a common spatially isolated volume;

a step of determining, from said shape groups, a target shape group for which said label corresponding to said bone is associated, predominantly, with said shapes of this group; and a step of selecting shapes from said target shape group.

14. The identification method of claim 11, further comprising surgically implanting an element of a prosthesis in the specific zone of the portion of bone of the patient, said method comprising:

the step of obtaining, by the medical imaging technique, the plurality of images representing parallel sections of the measurement volume comprising said portion of bone;

the step of automatically identifying the surface of said specific zone;

a step of connecting spatial location means to said portion of bone, said means associating the first coordinate system with said portion of bone;

a step of digitizing said specific zone;

a step of automatically registering said first coordinate system with the second coordinate system associated with the contours of said portion of bone identified from said plurality of images according to the initial parameters of the transfer matrix;

a step of connecting location means to said prosthetic element so as to provide the position and orientation of said prosthetic element relative to said first coordinate system; and a step of implantation, by a practitioner, of said prosthetic element in said specific zone within a spatial configuration determined at least from the representation of the position and contours of said prosthetic element and of at least said identified surface of said specific zone in said first coordinate system.

15. The method according to claim 14, wherein said bone is a bone of a joint, and in particular of the shoulder joint.

16. The according to claim 11, further comprising guiding a surgical tool for removing at least part of the portion of bone of the patient, wherein guiding comprises:

the step of obtaining, by the medical imaging technique, the plurality of images representing parallel sections of the measurement volume comprising said bone portion;

the step of automatically identifying the contours of said portion of bone from said plurality of images;

a step of connecting spatial location means to said portion of bone, said means associating the first coordinate system with said portion of bone;

a step of digitizing said specific zone;

a step of automatically registering said first coordinate system with the second coordinate system associated with said contours of said portion of bone identified from said plurality of images according to the initial parameters of the transfer matrix;

a step of connecting location means to said surgical tool so as to provide the position and orientation of said surgical tool relative to said first coordinate system; and a step of guiding said tool, at least from the representation of the position and contours of said tool and of said portion of bone in said first coordinate system.

* * * * *